Jan. 18, 1955 F. MEILLAND Plant Pat. 1,342
ROSE PLANT
Filed March 22, 1954
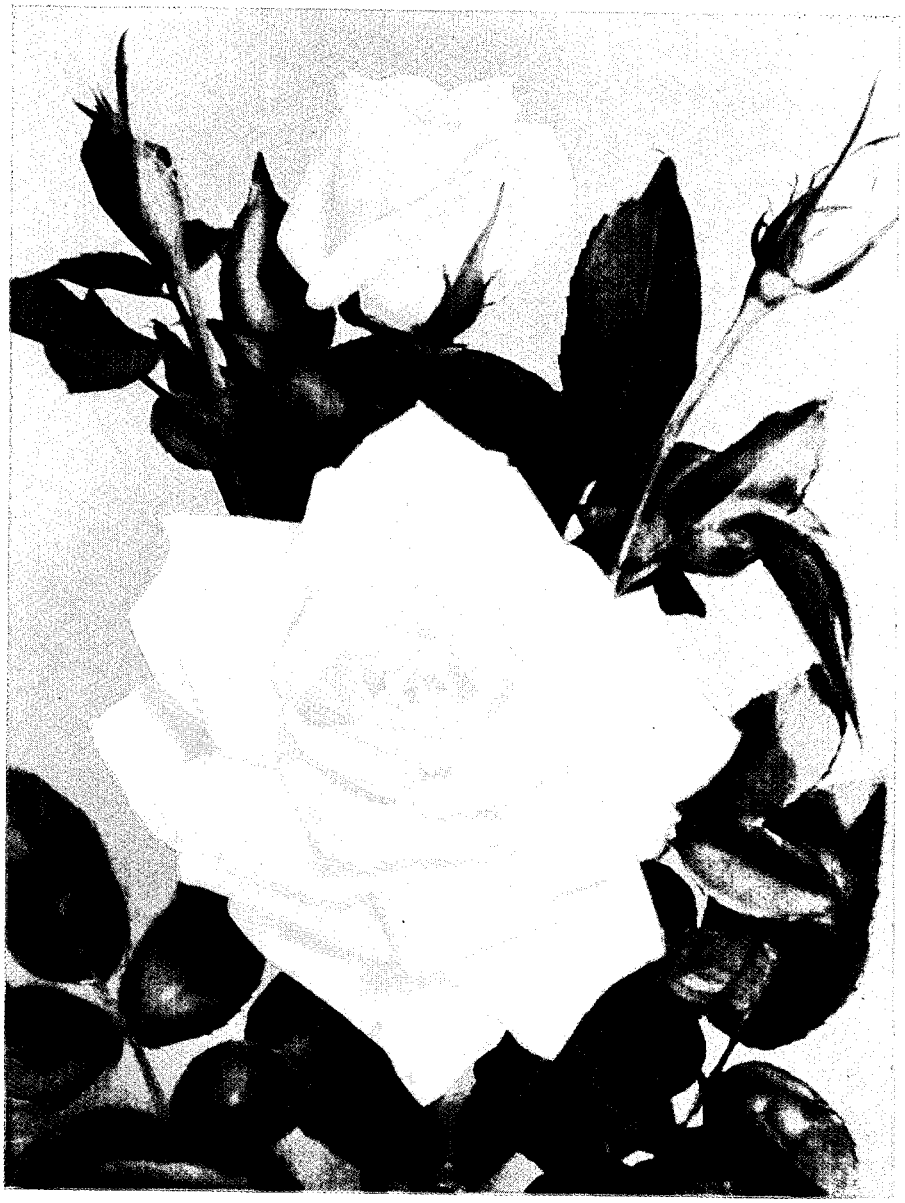
Inventor
Francis Meilland
By Robert Robb
Attorneys United States Patent Office Plant Pat. 1,342

Patented Jan. 18, 1955

1,342

ROSE PLANT

Francis Meilland, Cap Azura, Cap d'Antibes, France, assignor to The Conard-Pyle Company, West Grove, Pa., a corporation of Pennsylvania Application March 22, 1954, Serial No. 417,982

1 Claim. (Cl. 47—61)

The present invention relates to a new and distinct variety of rose plant of the hybrid tea class, which was originated by me by crossing the variety "Peace" (Plant Patent No. 591) with the variety "Duchess de Talleyrand" (unpatented).

As the result of this breeding, I have produced a new rose variety which is primarily characterized as to novelty by the unique general color effect of its blooms, which, from a distance, are Picric Yellow, shading into Martius Yellow at the outer edges of the petals. This color shading is not the result of fading, since the pale coloration is present in the newly opened flower, and does not spread over the entire petal even when the bloom has passed maturity. My new variety is also notable for its excellent vigor and freedom of bloom throughout the growing season. The above combination of features definitely differentiates this new variety from its parents, as well as from all other varieties of its class.

Asexual reproduction of my new variety by budding, as performed in France, as well as at West Grove, Pennsylvania, shows that the foregoing characteristics and distinctions come true to form and are established and transmitted through succeeding propagations.

The accompanying drawing shows typical specimens of the flowers and foliage of my new variety in different stages of development, and depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway") and the Royal Horticultural Society Color Chart (hereinafter abbreviated as "Royal") as indicated, except where general color terms of ordinary dictionary significance are obvious:

Type: Hardy; bush; outdoor; seedling; for cut-flowers and for garden decoration.
Class: Hybrid tea.
Breeding: Seedling.
*Seed parent.*—"Peace."
*Pollen parent.*—"Duchess de Talleyrand."
Propagation: Holds its distinguishing characteristics through suceeding propagations by budding.

FLOWER

Locality where grown and observed: West Grove, Pennsylvania.
Flowers borne: Singly; on medium length stems of normal strength.
Quantity of bloom: Free, outdoors.
Continuity: Continuous.
Fragrance: Moderate.
Bud:
*Peduncle.*—Medium length; medium caliper; stiff; rough; with numerous red prickles. Color—Claret Brown, Plate I (Ridgway), with Cosse Green, Plate V (Ridgway) on reverse.
*Before calyx breaks.*—Size—medium. Form—medium length; ovoid; with a conspicuous neck; with foliaceous appendages on the surface of the bud; with medium size, little-cut, bristle-like foliaceous parts extending beyond the tip of the bud equal to ¾ or more of its length.
*As calyx breaks.*—Color—Coral Red, Plate XIII (Ridgway).
*As first petal opens.*—Size—medium. Form—ovoid. Color: outside surface—Amber Yellow, Plate XVI (Ridgway), shading to Strontian Yellow, Plate XVI (Ridgway); inside surface—Straw Yellow, Plate XVI (Ridgway), shading to Citron Yellow, Plate XVI (Ridgway), and then to Lemon Chrome, Plate IV (Ridgway).

*Opening.*—Opens up well.
Bloom:
*Size* (when fully open).—Medium; from 3¼ inches to 3½ inches.
*Petalage.*—Double; from 38 to 52 broad petals; arranged regularly.
*Form.*—High-centered at first; becoming full and remaining high-centered; petals being at first tightly cupped, with the rim of the outer petals rolled outward; becoming later, at maturity, loosely cupped, with the rim of the petals rolled outward.
Petals: Medium thickness; soft; with inside satiny and outside shiny.
*Shape.*—Outer petals—obovate; usually with 1 notch, but sometimes more. Intermediate petals—obovate, with 1 notch. Inner petals—obovate, with 1 notch.

This description of a newly opened flower was made from a rose grown outdoors in the month of September, at West Grove, Pennsylvania:

*Color.*—Outer petal: outside surface—Marguerite Yellow, Plate XXX (Ridgway), shading to Light Chalcedony Yellow, Plate XVII (Ridgway), and then to Citron Yellow, Plate XVI (Ridgway) at base; inside surface—Marguerite Yellow, Plate XXX (Ridgway), shading to Pale Lemon Yellow, Plate IV (Ridgway) at base. Intermediate petal: outside surface—Barium Yellow, Plate XVI (Ridgway), shading to Citron Yellow, Plate XVI (Ridgway), with Strontian Yellow, Plate XVI (Ridgway) at base; inside surface—Martius Yellow, Plate IV (Ridgway), shading to Picric Yellow, Plate IV (Ridgway), and then to Strontian Yellow, Plate XVI (Ridgway) at base. Inner petal: outside surface—Barium Yellow, Plate XVI (Ridgway), shading to Citron Yellow, Plate XVI (Ridgway), and then to Strontian Yellow, Plate XVI (Ridgway); inside surface—Citron Yellow, Plate XVI (Ridgway), shading to Lemon Chrome, Plate IV (Ridgway).

This description was made from a rose that was open for three days outdoors in the month of September, at West Grove, Pennsylvania:

*Color.*—Outer petal: outside surface—Blanc Jaunatre, Tone 1, Plate 13 (Royal), shading to Pinard Yellow, Plate IV (Ridgway), and then to Empire Yellow, Plate IV (Ridgway); inside surface—Blanc Creme, Tone 2, Plate 10 (Royal), shading to Barium Yellow, Plate XVI (Ridgway), and then to Strontian Yellow, Plate XVI (Ridgway). Inner petal: outside surface—Straw Yellow, Plate XVI (Ridgway), shading to Amber Yellow, Plate XVI (Ridgway) at base; inside surface—Naphthalene Yellow, Plate XVI (Ridgway), shading to Barium Yellow, Plate XVI (Ridgway), and then to Pale Lemon Yellow, Plate IV (Ridgway).
*General color effect.*—Newly opened flower—Marguerite Yellow, Plate XXX (Ridgway). 3-days open—Naphthalene Yellow, Plate XVI (Ridgway).
*Behavior.*—Persist; fading Pale Yellow.
*Flower longevity.*—On bush in garden—3 days in September. Cut roses grown outdoors and kept at living-room temperatures—3 days in September.

REPRODUCTIVE ORGANS

Stamens: Medium number; arranged irregularly about pistils; mixed with petaloids; tucked in calyx.
Filaments: Most with anthers; medium length. Color—Lemon Chrome, Plate IV (Ridgway).
Anthers: All open at once; medium size; occasionally an anther fused with a petaloid. Color—Primuline Yellow, Plate IV (Ridgway).

Pollen: Sparse. Color—Light Cadmium, Plate IV (Ridgway).
Pistils: Medium number.
Styles: Uneven; medium length; medium caliper; bunched.
Stigma: Color—Pinard Yellow, Plate IV (Ridgway).
Ovaries: Some protruding from calyx.
Hips: None.
Sepals: Permanent; moderately long; spear-shaped.
Seeds: None.

PLANT

Foliage:

*Leaves.*—Compound of 5 and sometimes 7 leaflets; normal abundance; medium size; moderately thin; glossy.

*Leaflets.*—Shape—ovoid, with apex acute. Base—obtuse. Margin—simply serrate.

*Color.*—Mature: upper surface—Forest Green, Plate XVII (Ridgway); under surface—Asphodel Green, Plate XLI (Ridgeway); sometimes blotched with Deep Dull Yellow-Green, Plate XXXII (Ridgway). Young: upper surface—Haematite Red, Plate XXVII (Ridgway); under surface—Deep Livid Brown, Plate XXXIX (Ridgway).

*Rachis* (the supporting stem of the compound leaf).—Medium caliper.

Upper side—grooved; hairy and prickly.

Under side—moderately prickly and thorny.

*Stipules.*—Medium length; medium width; with medium length points turning out at an angle of more than 90°.

*Disease resistance.*—Normally resistant to blackspot, as compared with other varieties grown under comparable cultural conditions at West Grove, Pennsylvania.

Growth:

*Habit.*—Bushy; much-branched.

*Growth.*—Free.

*Canes.*—Medium caliper.

*Main stems.*—Color—Light Elm Green, Plate XVII (Ridgway). Thorns—several; medium length; slightly hooked downward. Prickles—several. Color—bronze. Hairs—none.

*Branches.*—Color—Parrot Green, Plate VI (Ridgway). Thorns—several; medium length; slightly hooked downward; with medium length, oval base. Prickles—several. Color—bronze. Hairs—few. Color—reddish.

*New shoots.*—Color—Victoria Lake, Plate I (Ridgway). Thorns—several; medium length; slightly hooked downward; with medium length, oval base. Prickles—few. Color—reddish. Hairs—none.

I claim:

A new and distinct variety of rose plant of the hybrid tea class, substantially as herein shown and described, characterized particularly as to novelty by its vigorous habit of growth and freedom of bloom throughout the growing season, and by the distinctive general color tonality of its blooms which appear from a distance as Picric Yellow, shading into Martius Yellow at the outer edges of their petals.

No references cited.